United States Patent [19]

Feiring

[11] Patent Number: 5,163,921
[45] Date of Patent: Nov. 17, 1992

[54] VALVED PERFUSION CARDIOVASCULAR CATHETERS

[76] Inventor: Andrew J. Feiring, 4454 N. Murray Ave., Milwaukee, Wis. 53211

[21] Appl. No.: 592,569

[22] Filed: Oct. 4, 1990

[51] Int. Cl.⁵ .............................................. A61M 5/00
[52] U.S. Cl. .................................... 604/247; 604/281
[58] Field of Search ............ 604/9, 247, 256, 280-282, 604/246; 137/852, 853, 855, 856, 859

[56] References Cited

U.S. PATENT DOCUMENTS

| | | | |
|---|---|---|---|
| 3,331,371 | 7/1967 | Rocchi et al. | 128/349 |
| 3,395,710 | 8/1968 | Stratton et al. | 128/350 |
| 3,592,184 | 7/1971 | Watkins | 604/247 |
| 3,726,283 | 4/1973 | Dye et al. | 604/247 |
| 3,888,249 | 6/1975 | Spencer | 128/214 |
| 3,995,617 | 12/1976 | Watkins et al. | 604/247 |
| 4,014,317 | 3/1977 | Bruno | 604/247 |
| 4,063,555 | 12/1977 | Ulinder | 137/853 |
| 4,468,224 | 8/1984 | Enzmann et al. | 604/247 |
| 4,549,879 | 10/1985 | Groshong et al. | 604/247 |
| 4,657,536 | 4/1987 | Dorman | 604/247 |
| 4,748,984 | 6/1988 | Patel | 128/658 |
| 4,753,640 | 6/1988 | Nichols et al. | 604/247 |
| 4,759,752 | 7/1988 | Stober | 604/247 |
| 4,820,271 | 4/1989 | Deutsch | 604/99 |
| 4,857,054 | 1/1989 | Helfer | 604/102 |
| 4,871,356 | 10/1989 | Haindl et al. | 604/247 |
| 5,030,210 | 7/1991 | Alchas | 604/247 |

Primary Examiner—C. Fred Rosenbaum
Assistant Examiner—Anthony Gutowski
Attorney, Agent, or Firm—Wolf, Greenfield & Sacks

[57] ABSTRACT

A guide catheter for use in coronary angioplasty, atherectomy and other cardiovascular interventions is provided with a side port having a one-way valve arrangement which permits the flow of aortic blood into the catheter lumen and out of the distal orifice of the catheter yet which closes in response to pressure injection of a liquid through the lumen of the catheter, such as injection of radiopaque contrast liquid. The valve element may be in the form of a thin flexible film constructed to be substantially immediately responsive to light pressure differentials across the valve element.

46 Claims, 4 Drawing Sheets

VALVED PERFUSION CARDIOVASCULAR CATHETERS

FIELD OF THE INVENTION

The invention relates to catheters used in cardiovascular diagnostic procedures as well as therapeutic procedures such as angioplasty, atherectomy and other similar cardiovascular procedures.

BACKGROUND OF THE INVENTION

Among the medical procedures performed by cardiologists is the angiographic examination of a patient's coronary arteries and treatment of those arteries by angioplasty to dilate or remove obstructions (stenoses) in the coronary arteries. The coronary arteries, which branch off the aorta, carry oxygenated blood back to the heart muscle itself to nourish and sustain the heart muscle (myocardium). The angiographic examination of the coronary arteries involves a brief injection of radiopaque contrast liquid. During the interval that the radiopaque contrast liquid is in the coronary arteries, the patient is observed under X-ray fluoroscopy. The radiopaque contrast liquid provides an X-ray image of the shape and anatomy of the patient's coronary arteries under investigation. Once the shape and anatomy of the coronary arteries, and the presence and nature of the stenosis has been determined, a balloon dilatation catheter or other type of angioplasty catheter is advanced to the site of the stenosis to dilate that portion of the artery or to remove the stenotic material.

In brief, the coronary angioplasty procedure involves the use of several catheters, guidewires and related devices. Initially, a guiding catheter is inserted percutaneously into the patient's arterial system, usually by a percutaneous puncture made in the femoral artery in the groin. The guide catheter is advanced, with the aid of a guidewire, upwardly through the patient's aorta to the region of the heart. The distal end (the end inside the patient) of the guide catheter is specially formed so that when it is disposed in the region of the heart, it will assume a shape that facilitates placement of the distal outlet tip of the catheter at the entrance to (the ostium) one of the two main coronary arteries. Typically, the distal tip of the guiding catheter will enter the ostium very slightly so as to be securely positioned. Once the guiding catheter has been so positioned, it provides a direct path for the subsequent balloon dilatation or other angioplasty catheters that are intended to enter into the coronary arteries to treat the stenosis.

In addition to providing a direct path to the entrance to the coronary arteries for purposes of inserting and removing angioplasty catheters, guidewires, and the like, the guide catheter also provides a means by which radiopaque contrast liquid may be injected into the coronary artery. Such injections and fluoroscopic examinations may be performed a number of times during an angioplasty procedure in order to examine and monitor the progress of the angioplasty treatment.

Conventional use of guide catheters in angioplasty and angiographic catheters in diagnostic procedures presents several problems. Among them is that when the distal tip of the catheter is firmly engaged with a narrowed coronary ostium, the catheter itself obstructs the flow of blood from the aorta into the coronary artery. It is necessary, of course, for blood to continue to flow into the coronary artery in order to nourish the myocardium and, for that reason, some catheters are provided with one or more side holes near the distal tip of the catheter by which blood can flow from the aorta through the side hole and the distal tip of the catheter into the coronary artery. The presence of such side holes, however, impairs the delivery of radiopaque contrast liquid to the coronary arteries. It is desired that the contrast liquid be injected into the coronary artery quickly and at a relatively high concentration so that the contrast liquid will spread throughout the coronary artery tree and remain in sufficient concentration to present a clear fluoroscopic image. If the concentration of contrast liquid is too low, the image may be weak and inadequate. When radiopaque contrast liquid is injected through a guide catheter having side holes, a significant portion of the contrast liquid may be emitted through the side holes and into the aorta, rather than into the coronary artery. Consequently, the flow rate and concentration of radiopaque contrast liquid entering the coronary artery is significantly reduced. In order to assure that there is a sufficient concentration of contrast media for sufficient visualization of the artery, typically it is necessary to increase the amount and injection rate of the contrast liquid. This results in injection of a significantly increased amount of contrast media into the patient's body which may have a detrimental effect on the patient.

There is a need, therefore, for cardiovascular catheters including guiding catheters and angiographic diagnostic catheters and other interventional cardiovascular catheters that enable flow of blood from the aorta into the coronary artery even while the guide catheter is intubated in the coronary ostium without impairing the ability of the guide catheter to deliver quickly contrast liquid in desirably high concentrations. There is also a need for interventional cardiovascular catheters possessing similar capabilities. It is among the general objects of the invention to provide such a guide catheter.

SUMMARY OF THE INVENTION

In order to overcome the foregoing difficulties, the invention is illustrated as being of incorporated into a guide catheter having a side port for admission of aortic blood into the catheter, but in which the side port is associated with a valve which normally remains open but which closes in response to injection of contrast liquid through the catheter. Preferably, the valve is of a flapper type, formed from a thin flexible film mounted within the wall of the guiding catheter. The side opening in the catheter is provided with a mesh through which blood may flow, the mesh being disposed exteriorly of the valve element to provide backing for the valve element when it is closed. Normally, the flapper valve element is kept open as a consequence of the differential pressure between the blood in the aorta and the catheter lumen. This permits blood to flow from the aorta into the central lumen of the catheter and out of the distal tip into the coronary artery. When contrast media is forced through the central lumen of the guide catheter, the pressure within the catheter is raised to a level well above aortic pressure which forces the flapper valve element outwardly against the mesh, thereby closing the side port and minimizing the loss of contrast liquid. After the contrast liquid has been injected, the pressure within the catheter lumen falls and the flapper valve returns to its open position under the influence of aortic blood pressure, once again permitting blood to flow from the aorta into the catheter.

It is among the general objects of the invention to provide an improved perfusion guiding catheter.

Another object of the invention is to provide a perfusion guiding catheter for use in coronary angioplasty and other cardiovascular interventions that allows perfusion of aortic blood through the catheter into the coronary artery, but which prevents emission of radiographic contrast liquid into the aorta during injection of contrast liquid.

Another object of the invention is to provide a perfusion guide catheter having a side port with a one way valve arrangement at the side port permitting flow into the lumen of the catheter.

A further object of the invention is to provide a valved perfusion guiding catheter of the type described in which the valve element may be shifted between open and closed positions under the influence of very low pressure differentials such that it may be opened under the influence of aortic blood pressure and closed rapidly in immediate response to pressure increase resulting from injection of contrast liquid.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENTS

Figure 1:
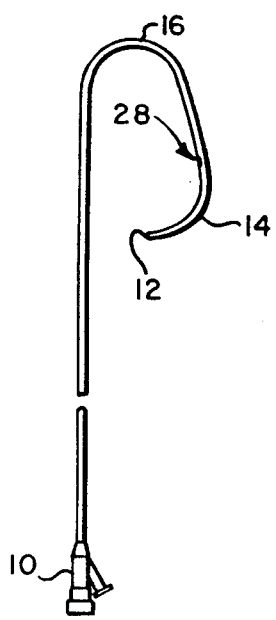
FIG. 1 is a somewhat diagrammatic, fragmented illustration of the shape of one type of guiding catheter, namely, a "Judkins left" catheter adapted to intubate the left coronary artery.
Figure 2:
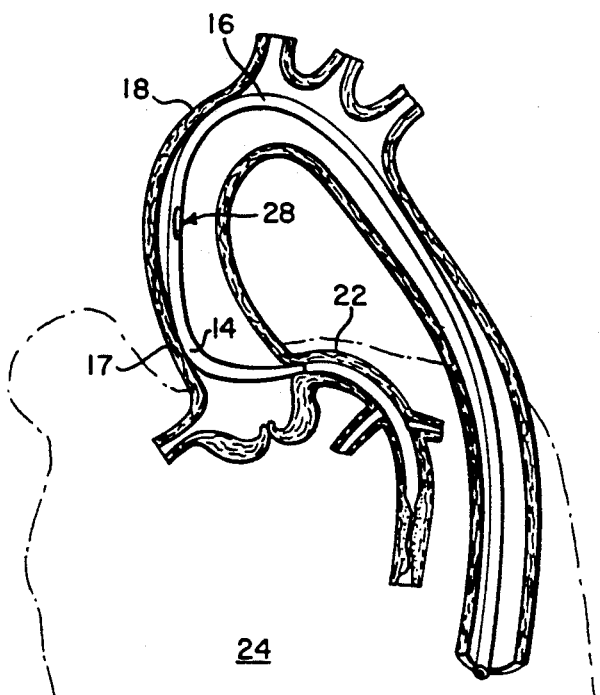
FIG. 2 is a somewhat diagrammatic illustration of the anatomy in the region of the aortic arch and the heart illustrating, diagrammatically, the manner in which the Judkins left guidingcatheter of FIG. 1 resides in the region when the distal tip of the guide catheter engages the coronary ostium.

FIG. 1 illustrates, diagrammatically, the configuration of one type of guiding catheter, referred to as a "Judkins left" catheter. The Judkins left catheter is intended to facilitate intubation of the left main coronary artery 22 (FIG. 2). The catheter has a proximal end and a distal end, the proximal end having a fitting 10, such as luer fitting, adapted to be connected to various devices that may be used in the angioplasty procedure, such as a syringe for injecting radiopaque contrast liquid (not shown). The distal end of the catheter that is inserted into the patient is specially curved so that when it is located in the region of the aortic arch 18 (FIG. 2), the distal tip 12 will engage the coronary ostium. More particularly, the Judkins left catheter configuration includes a primary curve 14 and a secondary curve 16.

FIG. 2 illustrates the manner in which the distal end of the guide catheter shown in FIG. 1 resides in the aortic arch and the region of the coronary ostium. When the catheter is placed and seated, the curved distal end assumes a more opened configuration where it passes through the aortic arch 18. The configuration is such that the primary and secondary curves 14, 16 will engage the ascending aorta 17 and the aortic arch 18 generally as shown, with the tip 12 in engagement with the left coronary ostium 20 of the left main coronary artery 22. The left main coronary artery branches out into a many branched "coronary tree" (not shown) which feeds oxygenated blood directly to the myocardium 24.

Figure 3:
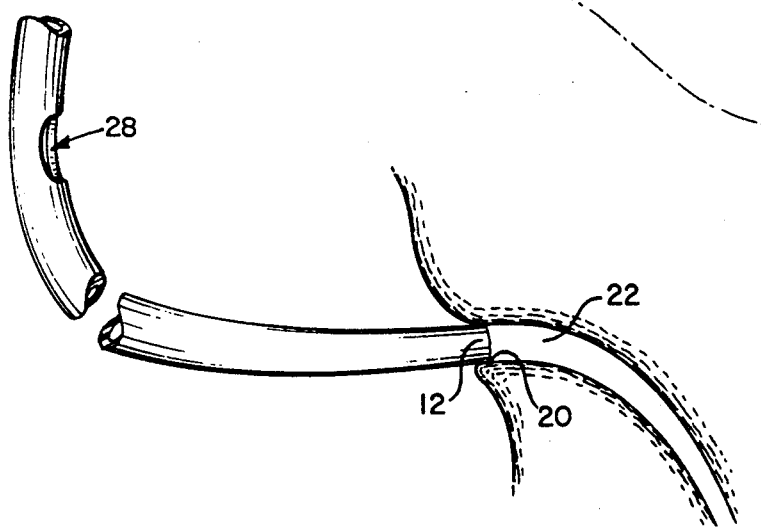
FIG. 3 is an enlarged diagrammatic illustration of the engagement of the distal tip of the guiding catheter in engagement with the coronary ostium.

FIG. 3 illustrates the engagement of the distal tip 12 of the guide catheter with the coronary ostium 20 of the left main coronary artery 22. FIG. 3 also illustrates, in phantom, the location of a typical side hole 28 in a conventional guiding catheter. The side hole 28 communicates with the central lumen of the guide catheter and enables blood to flow from the aorta into the coronary artery to maintain a flow of blood into the coronary artery. Once the guide catheter is in place, it provides quick, a traumatic and ready access to the coronary artery so that successive smaller diameter angioplasty catheters and related guidewires may be inserted into and removed from the coronary artery with ease and minimal delay.

In accordance with the invention, the distal tip region of the catheter is not provided with the typical side hole. Instead, the catheter is provided with a side flow port, indicated generally at 28 (see also FIGS. 4-6). In the Judkins left catheter illustrated, the flow port 28 preferably is formed between the primary curve 14 and the secondary curve 16. The flow port 28 is associated with a one-way valve arrangement which, as described above, enables flow from the aorta into the catheter under normal aortic blood pressure, but which will close under the influence of pressure developed when radiographic contrast liquid is injected into the catheter.

Figure 4:
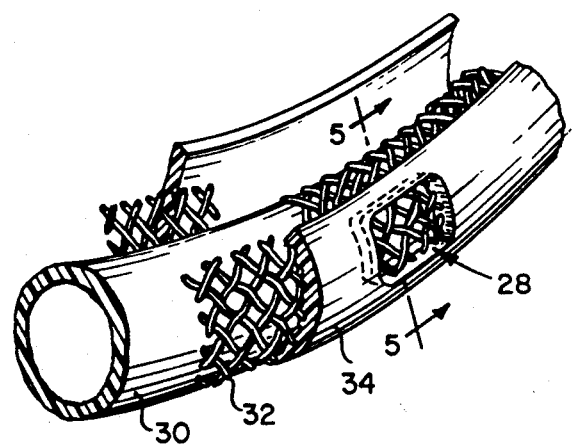
FIG. 4 is a partly broken away, partly sectional illustration of a segment of the guiding catheter, including the valved side port, and illustrating the multi layered construction of the catheter.
Figure 5:
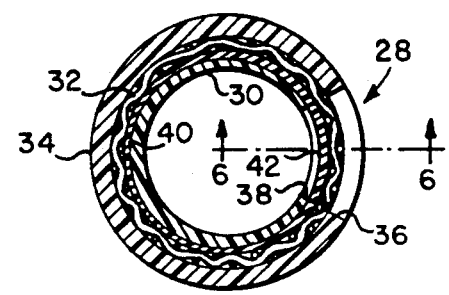
FIG. 5 is a sectional illustration through the catheter at the valved side hole portion, as seen at the plane 5—5 of FIG. 4.

FIG. 4 illustrates the construction of the catheter shaft in one type of guide catheter that may be used in the practice of the invention. As shown, the shaft may be formed from an inner polymeric tubular layer 30, such as Teflon (polytetrafluoroethylene). A tubular braided mesh 32 which may be formed from metallic or polymeric strands overlies the inner Teflon layer 30. The helical braided mesh 32 serves to enhance the torsional stiffness of the catheter so that its distal end may be rotated within the patient by manipulation of the exposed proximal end. Such manipulation is necessary in order to properly advance and seat the catheter in the manner illustrated in FIG. 2. The catheter shaft then is provided with an outer polymeric layer 34 which may be formed from an appropriate material such as polyurethane. The polyurethane may be sprayed or otherwise applied to the shaft. Guiding catheters having such shaft construction are commercially available from companies such as U.S.C.I. Division of C. R. Bard, Inc., Murray Hill, N.J.

In accordance with the invention, port 28 is formed by forming an aperture 36 in the outer layer 34 and an aperture 38 in the inner layer 30 of the catheter. The outer and inner apertures 36, 38 are in registry with each other. The braided mesh 32, however, remains intact and extends across the port 28 defined by the aligned apertures 36, 38. The mesh is sufficiently open to enable blood to flow through the port 28 from the aorta into the central lumen of the catheter.

Figure 4A:
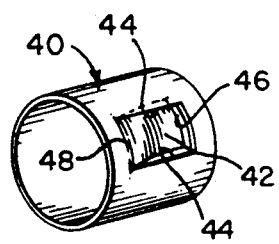
FIG. 4A is an illustration of one type of valving element that may be used in the invention.

In accordance with the invention, a valving element is provided in association with the port 28. FIG. 4A illustrates one form of the valving element and its supporting structure. As shown in this embodiment, the arrangement includes a film of thin, flexible sheet material, such as an appropriate polymer formed into a ring configuration 40. The ring 40 is provided with a cut-out segment 42 which defines the movable valve element. In the embodiment shown in FIGS. 4–6, the movable valve element is defined by a pair of side slits 44 and an end slit 46. The other end is unslit and defines a flexible hinge line, indicated in phantom at 48. The ring 40 may be incorporated into the catheter during the layer by layer buildup of the catheter by placing the ring over the inner layer 30 and between the inner layer 30 and the braided mesh 32. The ring 40 is placed so that the movable valve element 42 is in registry with the flow port 28, the valve element 42 being oriented so that the hinge line 48 is not disposed at the distal end of the port 28, that is, the hinge line is located at the proximal end or parallel to the sides of the port 28.

The material from which the valve element is formed should have a high tensile strength yet be extremely thin and light so that it responds substantially instantaneously to changes in pressure and offers no significant resistance to flow. The ring and movable valve element 40, 42 preferably are formed from thin sheet material, for example, from polyethylene terephthalate (Mylar) sheet and may be of a thickness of the order of 0.0001 to 0.001 inches. Such material displays sufficient toughness and flex life as to avoid being torn in use, as catheters and guidewires are passed through the guide catheter.

Figure 6:
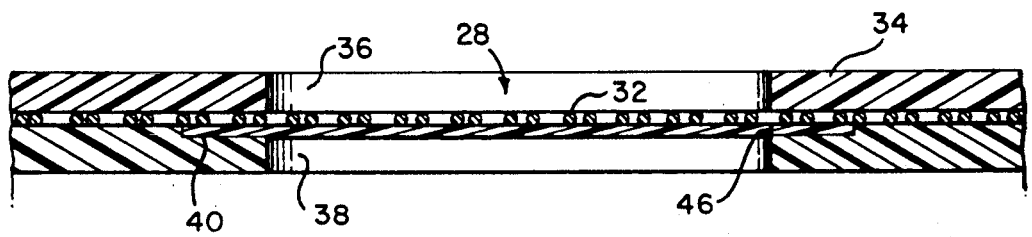
FIG. 6 is a greatly enlarged sectional illustration of the region of the valved side port as seen at the plane 6—6 of FIG. 5, and with the valve element in a closed configuration.
Figure 7:
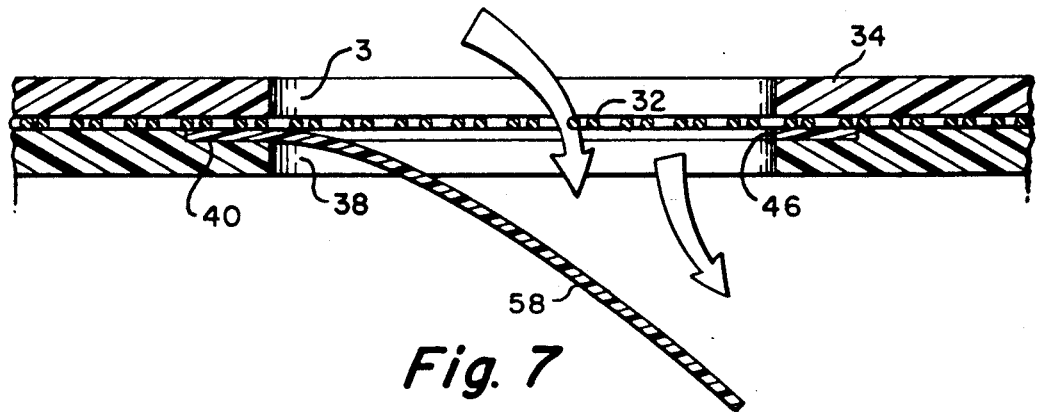
FIG. 7 is an illustration similar to FIG. 6 showing the valve element in an open configuration, having been opened under the influence of arterial blood pressure.

The operation of the valve element is illustrated in FIGS. 6 and 7 which show the valve element closed and open, respectively. FIG. 6 illustrates the configuration of the valve element when contrast liquid is being injected under pressure (that is, the pressure of the liquid is greater than the ambient arterial positive pressure) into the guide catheter. It will be appreciated that under the influence of such positive pressure, the valve element 42 will be pressed outwardly against the braided mesh 32 within the port 28, thereby effectively blocking off flow of contrast liquid out of the catheter. Consequently, all of the contrast liquid is delivered to the coronary artery, resulting in adequate concentration for proper fluoroscopic visualization without flooding the patient's system with large quantities of contrast liquid. FIG. 7 illustrates the configuration of the movable valve element 42 in an open configuration, under the influence of normal positive aortic blood pressure (that is, when the ambient arterial blood pressure is greater than the pressure in the lumen of the catheter). As shown, the valve element flexes along the hinge line 48 to an open configuration such that blood can flow from the aorta into the lumen of the guide catheter, as suggested by the arrows 50. The mass of the movable valve element 42 is extremely low, being formed from very thin flexible film and, therefore, can open easily under the influence of a very light pressure differential across the valve element, resulting from normal aortic blood pressure.

Figure 8:
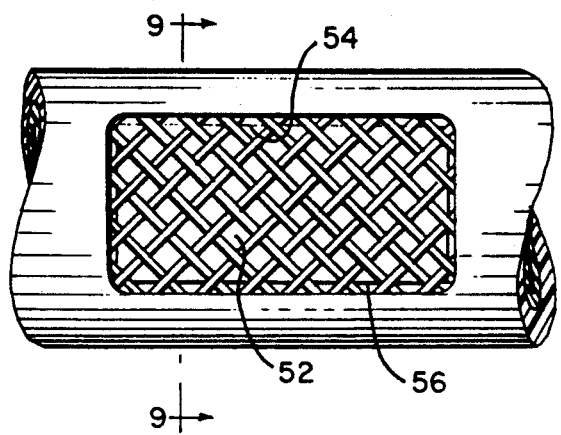
FIG. 8 is an illustration of the valved side port portion of the catheter as seen from outside of the catheter in which the flapper valve is hinged along its side, along a hinge line generally parallel to the axis of the catheter.
Figure 9:
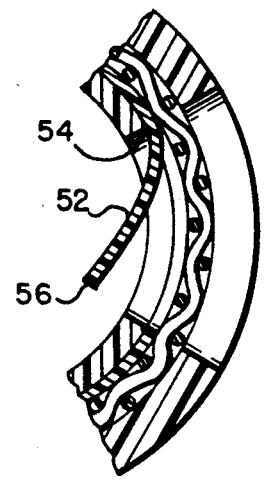
FIG. 9 is a sectional illustration of the valved side port of FIG. 8 as seen along the plane 9—9 of FIG. 8, illustrating the valved element in an open configuration under the influence of aortic pressure.

FIGS. 8 and 9 illustrate another preferred embodiment of the valve element in which the movable valve element 42 is cut so that the hinge line 52 extends lengthwise of the axis of the catheter. In this, a preferred embodiment, the hinge line 54 extends longitudinally of the catheter, as does the free edge 56. This embodiment, as the other embodiments, operates in similar fashion, in that the valve element 52 will open, as shown in FIG. 9, under the influence of a light pressure differential from the aortic blood pressure, yet will close immediately when contrast liquid is injected into the lumen of the catheter, thereby raising the pressure within the catheter lumen above the aortic blood pressure.

Figure 10:
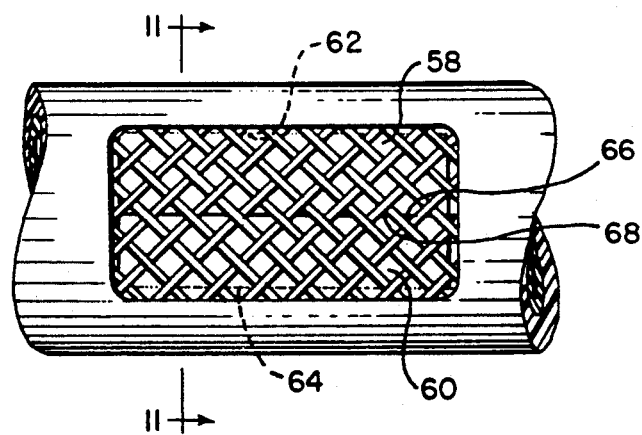
FIG. 10 is an illustration similar to FIG. 8 of another embodiment of the valving arrangement in which the valve element includes a pair of flaps each hinged along a longitudinally-extending hinge line.
Figure 11:
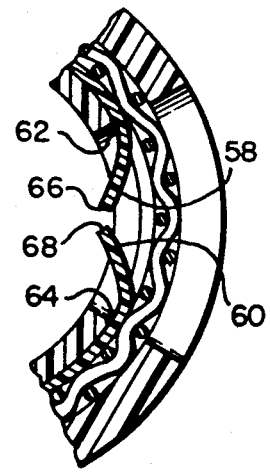
FIG. 11 is an illustration seen along the plane 11—11 of FIG. 10 showing the flap valve in an open configuration under the influence of aortic pressure.
Figure 12:
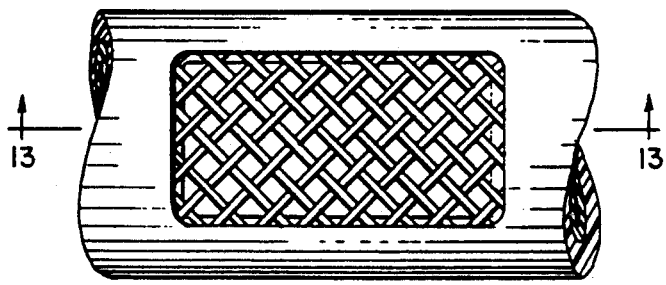
FIG. 12 is an illustration similar to FIG. 8 of another embodiment of a valved side port in which the valve element is initially sealed closed and which may be freed for operation by aspirating the guide catheter slightly.

FIGS. 10 and 11 illustrate still another embodiment of the valving arrangement in which a pair of hinged valve elements 58, 60 are formed in the sheet material, each of the valve elements 58, 60 having a hinge line 62, 64 and free edge 66, 68, respectively. In this embodiment, the width of each of the valve element flaps is reduced to reduce the extent to which the flaps will project into the guidewire lumen, thereby reducing the chance of interference with catheters and guidewires that may be passed through the guide catheter. Each of the valve elements 58, 60 operates in the same way as the above described valve elements in that they will open, as shown in FIG. 11, under the influence of positive aortic blood pressure and will close under the influence of higher injection pressure of contrast liquid.

Figure 13C:
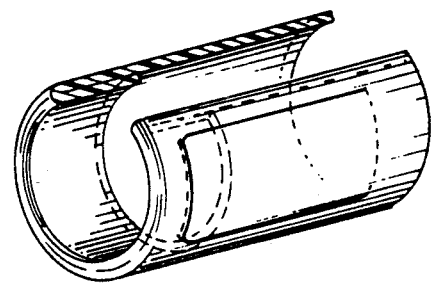
FIG. 13C is an illustration of a band of thin polymeric material formed to define the valving configuration of FIGS. 13A and 13B.
Figure 13A:
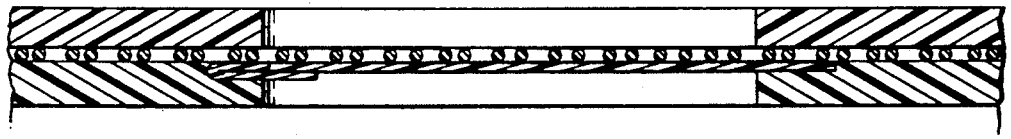
FIG. 13A is a sectional illustration through the valved side port of FIG. 12 as seen along the plane 13—13.
Figure 13B:
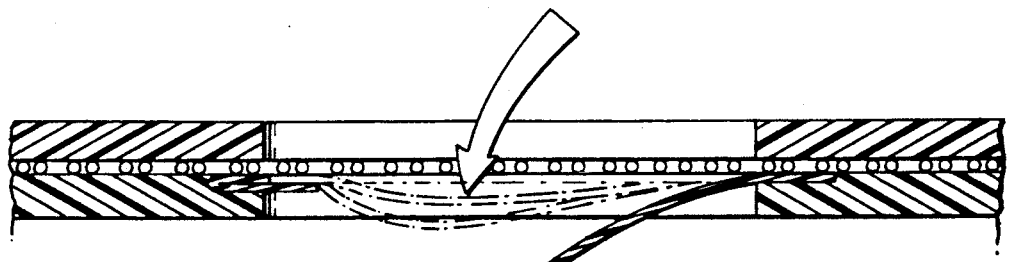
FIG. 13B is an illustration of the valved side port of FIG. 13 illustrating the manner in which the valve element is freed from its initially closed position.

FIGS. 12 and 13A–13C illustrate a modified embodiment of the invention in which means are provided for initially maintaining the valve element in a closed configuration so that it will not open under the influence of aortic blood pressure. In that configuration, it may be possible to make coronary or arterial pressure measurement through the guide catheter. In this embodiment, the ring, shown in FIG. 13C, is folded over about itself to define an overlapped region. The valve element, however, is not folded over and, therefore, overlies the folded over region. When the catheter is assembled, a marginal portion of the free edge of the valve element is placed to be disposed between the folded over region of the sheet material and the mesh layer. In that configuration, the free edge will be retained in a position as to obstruct the port and preclude flow through the port. In this configuration, the guide catheter acts as an unapertured catheter, thereby permitting pressure measurements to be made and the like. Additionally, radiopaque contrast liquid may be injected in that configuration. Should it be desired to free the valve element so that it can open under the influence of aortic blood pressure, thereby enabling aortic blood to perfuse into the catheter and to the coronary arteries, that may be accomplished by applying suction to the proximal end of the guide catheter. The application of suction will draw the free valve element out from engagement between the folded portion of the film and the mesh and, thereafter, the valve element will function in the same manner described above in connection with the other embodiments.

It is preferred to place the valved port 28 between the primary curve 14 and the secondary curve 16 on the inside of the curve of both left and right Judkins catheters. By so locating the valved port 28, the widest possible clearance between the flapper valve and the angioplasty catheters and guidewires is provided when the valve element is open. It also may be desirable to locate the valve immediately before the secondary curve on the left Judkins and between the primary and secondary curve with the right Judkins catheter. The reason for this is that during PTCA the physician may try to shape and bend the guiding catheter by pushing it against the aortic arch. This can result in buckling of the catheter between the primary and secondary curves. It is possible that locating the port in the region of potential buckling could weaken the structure of the catheter and make it more prone to buckling. Thus, in order to avoid that problem, it may be necessary to place the port on the right coronary artery further back (in a proximal direction) than the usual location of a conventional open side hole. It should be understood, however, that the braided tubular layer may provide sufficient resistance to buckling and, in that case, there may be more latitude in the location of the flow port 28.

The dimensions of the flapper valves and perfusion ports depend on the volume of conduit flow desired. A typical 0.078 inch inner diameter lumen guiding catheter (nominally 2 mm diameter) has a lumen cross sectional area of about 3.14 square millimeters. Thus, it would desirable to match the cross sectional flow area of the valve port 28 to the cross sectional flow area of the catheter lumen. Consequently, by way of example, a rectangular perfusion port may be formed that will have the dimensions of 0.5 mm wide and 6.28 mm long, or 0.25 mm by 12.5 mm. Alternately, two or more valved ports may be placed at several sites with the dimensions at each being correspondingly smaller, the combined flow area corresponding to the flow area of the catheter lumen. For example, two ports having valves 0.125 mm by 12.5 mm. It is preferable to maintain the width of the flapper valve relatively narrow so that it will not protrude excessively into the guide catheter lumen and will not become caught on the PTCA equipment.

From the foregoing, it will be appreciated that I have provided an improved cardiovascular catheter structure that may be used in coronary angioplasty as well as in guide catheters used in coronary and peripheral angioplasty atherectomy and other cardiovascular interventions as well as in angiographic diagnostic catheters. The catheter permits aortic blood to flow into the catheter and out of the distal end of the catheter to perfuse the coronary arteries. It permits such perfusion, however, in a manner that does not impair the effectiveness of contrast liquid injection and, particularly, does not require that large volumes of contrast liquid be injected into the patient. Substantially all of the contrast liquid injected into the guide catheter is delivered to the coronary artery. It should be understood, however, that the foregoing description of the invention is intended merely to be illustrative thereof and that other embodiments, modifications and equivalents may be apparent to those skilled in the art without departing from its spirit.

Having thus described the invention, what I have desired to claim and secure by Letters Patent is:

1. A cardiovascular catheter comprising:
   an elongate flexible tubular shaft having a proximal end, a distal end, a proximal portion adapted to be disposed outside of the patient and a distal portion adapted to be placed within the patient, and a lumen extending from the proximal end to an outlet orifice at the distal tip of the shaft, the lumen being substantially unobstructed;
   a side port formed in the wall of the tubular shaft at a location proximal of the distal tip, and in the distal portion of the shaft; and
   a valve element disposed in the side port and being adapted to open when the pressure of the aortic blood proximal to the port on the outside of the wall exceeds the pressure interiorally of the lumen of the catheter, and to close when the pressure of liquid within the lumen of the catheter exceeds the pressure of the aortic blood in the region of the side port.

2. A catheter as defined in claim 1 wherein the distal end of the catheter is curved and where the side port is formed on the inside of the curve.

3. A catheter as defined in either of claims 1 or 2 wherein the catheter comprises a Judkins left catheter having a primary curve and a secondary curve and the port is located between the primary curve and the secondary curve.

4. A catheter as defined in claim 3 wherein the catheter comprises a guide catheter for guiding an angioplasty catheter.

5. A catheter as defined in either of claims 1 or 2 wherein the catheter comprises a Judkin s right catheter having a primary curve and secondary curve and the port is dispose between the primary and secondary curves of the catheter.

6. A catheter as defined in claim 5 wherein the catheter comprises a guide catheter for guiding an angioplasty catheter.

7. A catheter as defined in claim 1 wherein the valve element comprises a flexible film element mounted to the catheter wall in obstructing relation to the said port and being flexible along a hinge line between open and closed configurations.

8. A catheter as defined in claim 7 wherein the catheter wall includes a perforate support element extending over the said port, the flexible film element being located interiorally of the catheter with respect to the perforate support element.

9. A catheter as defined in claim 8 wherein the catheter wall includes a braided tubular sheath, said sheath defining the perforate support element.

10. A catheter as defined in claim 8 wherein the catheter wall includes inner and outer layers and the perforate support element is disposed between the inner and outer layers.

11. A catheter as defined in claim 9 wherein the catheter wall includes inner and outer layers and the braided sheath is disposed between said inner and outer layers.

12. A catheter as defined in any one of claims 1 or 7-11 wherein the valve element is formed in a film formed into a ring, the ring being mounted in the wall of the catheter, the valve element being defined by a flap valve cut into the film.

13. A catheter as defined in claim 7 wherein the film comprises a polymeric material having a thickness of the order of 0.0001"-0.001".

14. A catheter as defined in claim 12 wherein the film comprises a polymeric material having a thickness of the order of 0.0001"-0.001".

15. A catheter as defined in claim 13 wherein the film comprises polyethylene terephthalate.

16. A catheter as defined in claim 14 wherein the film comprises polyethylene terephthalate.

17. A catheter as defined in claim 7 wherein the valve element is formed to define a hinge line located at the proximal end of the valve element.

18. A catheter as defined in claim 7 wherein the valve element is formed to include a hinge line that extends parallel to the longitudinal dimension of the catheter.

19. A catheter as defined in claim 7 wherein the valve element is formed by an H-shaped slit defining a pair of flaps, each flap having a hinge line extending parallel to the longitudinal dimension of the catheter.

20. A catheter as defined in claim 12 wherein the valve element is formed to define a hinge line located at the proximal end of the valve element.

21. A catheter as defined in claim 12 wherein the valve element is formed to include a hinge line that extends parallel to the longitudinal dimension of the catheter.

22. A catheter as defined, in claim 12 wherein the valve element is formed by an H shaped slit defining a pair of flaps, each flap having a hinge line extending parallel to the longitudinal dimension of the catheter.

23. A catheter as defined in claim 1 further comprising:
means for initially maintaining the valve element in a closed configuration independently of positive aortic blood pressure or positive pressure of liquid injected into the lumen, said means being constructed to enable the valve element to be released from said initially closed position.

24. A catheter as defined in claim 23 wherein said means comprises said valve element being responsive to aspiration applied to the lumen of the catheter to dislodge the valve element from said initially closed position.

25. A catheter as defined in claim 23 wherein the valve element is formed in a film of polymeric material formed into a ring and mounted in the wall of the catheter, the valve element being cut from the ring to define a flap-like element having a free end, the ring having a folded portion adapted to underlie the free end of the valve element in a manner as to maintain the valve element in an initially closed position.

26. A catheter as defined in any one of claims 1, 2, 7-11, 13, 15, 17, 19 and 23-25 wherein the catheter comprises a guide catheter adapted for use as an adjunct to angioplasty.

27. A catheter as defined in any one of claims 1, 2, 7-11, 13, 15, 17, 19 an 23-25 wherein the catheter comprises a diagnostic angiographic catheter.

28. A catheter as defined in claim 12 wherein the catheter comprises a guide catheter adapted for use as an adjunct to angioplasty.

29. A catheter as defined in claim 12 wherein the catheter comprises a diagnostic angiographic catheter.

30. A catheter as defined in claim 20 wherein the catheter comprises a guide catheter usable as an adjunct to angioplasty.

31. A catheter as defined in claim 20 wherein the catheter comprises a diagnostic angiographic catheter.

32. A catheter as defined in claim 21 wherein the catheter comprises a guide catheter adapted for use as an adjunct to angioplasty.

33. A catheter as defined in claim 21 wherein the catheter comprises a diagnostic angiographic catheter.

34. A catheter as defined in claim 22 wherein the catheter comprises a guide catheter adapted for use as an adjunct to angioplasty.

35. A catheter as defined in claim 22 wherein the catheter comprises a diagnostic angiographic catheter.

36. A cardiovascular catheter as defined in claim 1 wherein the catheter comprises an vatherectomy catheter.

37. A cardiovascular catheter as defined in claim 1 wherein the catheter comprises an interventional cardio vascular catheter.

38. A catheter for coronary angioplasty comprising:
an elongate flexible tubular shaft having a proximal end; a distal end, a proximal portion adapted to be disposed outside of the patient and a distal portion adapted to be placed within the patient, and a lumen extending from the proximal end to an outlet orifice at the distal tip of the shaft, the lumen being substantially unobstructed;
a side port formed in the wall of the tubular shaft at a location proximal of the distal tip, and in the distal portion of the shaft; and
one-way valve means associated with the side port for enabling aortic blood flow into the lumen of the catheter when the pressure of the aortic blood in the region of the port outside of the wall exceeds the pressure within the lumen of the catheter and to preclude flow through the port when the pressure of the liquid within the lumen of the catheter exceeds the pressure of the aortic blood in the region of the port.

39. A catheter as defined in claim 38 wherein the catheter comprises a guide catheter used as an adjunct to an angioplasty procedure.

40. A catheter as defined in claim 38 wherein the catheter comprises a diagnostic angiographic catheter.

41. A method for effecting perfusion of a coronary artery during an angiographic examination of the coronary artery comprising:
providing an elongate flexible tubular shaft having a proximal end, a distal end, a proximal portion adapted to be disposed outside of the patient and a distal portion adapted to be placed within the patient, and a lumen extending from the proximal end to an outlet orifice at the distal tip of the shaft, the lumen being substantially unobstructed; a side port formed in the wall of the tubular shaft at a location proximal of the distal tip, and in the distal portion of the shaft; and a valve element disposed in the side port and being adapted to open when the pressure of the aortic blood proximal to the port on the outside of the wall exceeds the pressure interiorally of the lumen of the catheter, and to close when the pressure of liquid within the lumen of the catheter exceeds the pressure of the aortic blood in the region of the side port;

placing the catheter in the patient's arteries with the distal tip of the catheter disposed at a coronary ostium;

at least once during the procedure, injecting radiopaque contrast liquid through the lumen of the catheter into the coronary artery under pressures sufficient to close the valve element such that after said step of injection is terminated, the ambient blood pressure about the catheter will cause the valve element to open thereby restoring perfusion flow of blood into the lumen of the catheter and out of its distal orifice into the coronary artery.

42. A method as defined in claim 41 further comprising said valving element being constructed to be retained in an initially closed position independently of the positive ambient blood pressure or injection pressure, said method further comprising:

before permitting the valve element to open to permit perfusion flow, perform blood pressure measurements through the catheter; and thereafter aspirating the lumen of the guide catheter to release the valve element to permit perfusion flow through the port.

43. A method as defined in claim 41 wherein the catheter comprises a guide catheter used as an adjunct to an angioplasty procedure.

44. A method for effecting perfusion of a coronary artery during coronary angioplasty of the coronary artery comprising:

providing an elongate flexible tubular shaft having a proximal end, a distal end, a proximal portion adapted to be disposed outside of the patient and a distal portion adapted to be placed within the patient, and a lumen extending from the proximal end to an outlet orifice at the distal tip of the shaft, the lumen being substantially unobstructed; a side port formed in the wall of the tubular shaft at a location proximal of the distal tip, and in the distal portion of the shaft; and a valve element disposed in the side port and being adapted to open when the pressure of the aortic blood proximal to the port on the outside of the wall exceeds the pressure interiorally of the lumen of the catheter, and to close when the pressure of liquid within the lumen of the catheter exceeds the pressure of the aortic blood in the region of the side port;

placing the catheter in the patient's arteries with the distal tip of the catheter disposed at a coronary ostium;

at least once during the procedure, injecting radiopaque contrast liquid through the lumen of the catheter into the coronary artery under pressures sufficient to close the valve element such that after said step of injection is terminated, the positive ambient blood pressure about the catheter will cause the valve element to open thereby restoring perfusion flow of blood into the lumen of the catheter and out of its distal orifice into the coronary artery.

45. A method as defined in claim 44 further comprising said valving element being construed to be retained in an initially closed position independently of the positive ambient blood pressure or injection pressure, said method further comprising:

before permitting the valve element to open to permit perfusion flow, perform blood pressure measurements through the catheter; and thereafter aspirating the lumen of the guide catheter to release the valve element to permit perfusion flow through the port.

46. A method as defined in claim 44 wherein the catheter comprises a guide catheter used as an adjunct to an angioplasty procedure.

* * * * *